United States Patent
Studer

(10) Patent No.: US 10,799,107 B2
(45) Date of Patent: Oct. 13, 2020

(54) OPHTHALMOLOGICAL PATIENT INTERFACE

(71) Applicant: Ziemer Ophthalmic Systems AG, Port (CH)

(72) Inventor: Thomas Studer, Neuchâtel (CH)

(73) Assignee: Ziemer Ophthalmic Systems AG, Port (CH)

( * ) Notice: Subject to any disclaimer, the term of this patent is extended or adjusted under 35 U.S.C. 154(b) by 223 days.

(21) Appl. No.: 15/866,149

(22) Filed: Jan. 9, 2018

(65) Prior Publication Data

US 2018/0160895 A1 Jun. 14, 2018

(30) Foreign Application Priority Data

Nov. 18, 2016 (EP) ..................................... 16199582

(51) Int. Cl.
*A61B 3/00* (2006.01)
*A61F 9/009* (2006.01)
*A61F 9/008* (2006.01)

(52) U.S. Cl.
CPC ............ *A61B 3/0083* (2013.01); *A61F 9/009* (2013.01); *A61B 3/0075* (2013.01); *A61F 2009/00865* (2013.01); *A61F 2009/00872* (2013.01)

(58) Field of Classification Search
CPC ....... A61B 3/0083; A61B 3/0075; A61B 3/00; A61F 9/009; A61F 2009/00872; A61F 2009/00865; A61F 9/008
See application file for complete search history.

(56) References Cited

U.S. PATENT DOCUMENTS

| | | | | |
|---|---|---|---|---|
| 6,497,700 B1* | 12/2002 | LaHaye | ............... | A61F 9/00802 606/4 |
| 6,730,074 B2* | 5/2004 | Bille | ................... | A61F 9/00825 128/898 |
| 2004/0036839 A1* | 2/2004 | Fischer | ................... | A61F 9/009 351/219 |
| 2007/0093796 A1* | 4/2007 | Raksi | ...................... | A61F 9/009 606/10 |
| 2011/0022035 A1* | 1/2011 | Porter | ..................... | A61F 9/009 606/4 |
| 2013/0053837 A1* | 2/2013 | Kandulla | ................. | A61F 9/009 606/4 |
| 2014/0222050 A1* | 8/2014 | Heitel | ..................... | A61F 9/009 606/166 |

FOREIGN PATENT DOCUMENTS

| | | |
|---|---|---|
| EP | 1731120 B1 | 5/2008 |
| EP | 2853247 B1 | 7/2016 |
| WO | 2012031277 A1 | 3/2012 |

* cited by examiner

*Primary Examiner* — Gary Jackson
*Assistant Examiner* — Sebastian X Lukjan
(74) *Attorney, Agent, or Firm* — Banner & Witcoff, Ltd.

(57) ABSTRACT

Disclosed is a patient interface for affixment on onto a patient eye, said patient interface including
a negative pressure cavity with a top wall and a circumferential outer wall,
an optical passage,
wherein the top wall circumferentially surrounds the optical passage and wherein the circumferential outer wall projects from the top wall and circumferentially surrounds the optical passage;
a number of rib members, the rib members projecting separately from each other from the top wall into the negative pressure cavity between the circumferential outer wall and the optical passage.

19 Claims, 4 Drawing Sheets

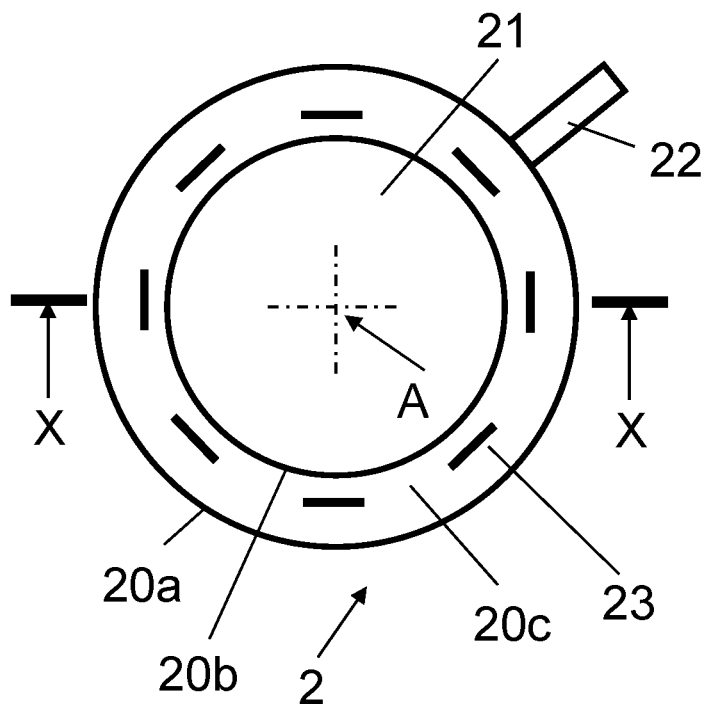
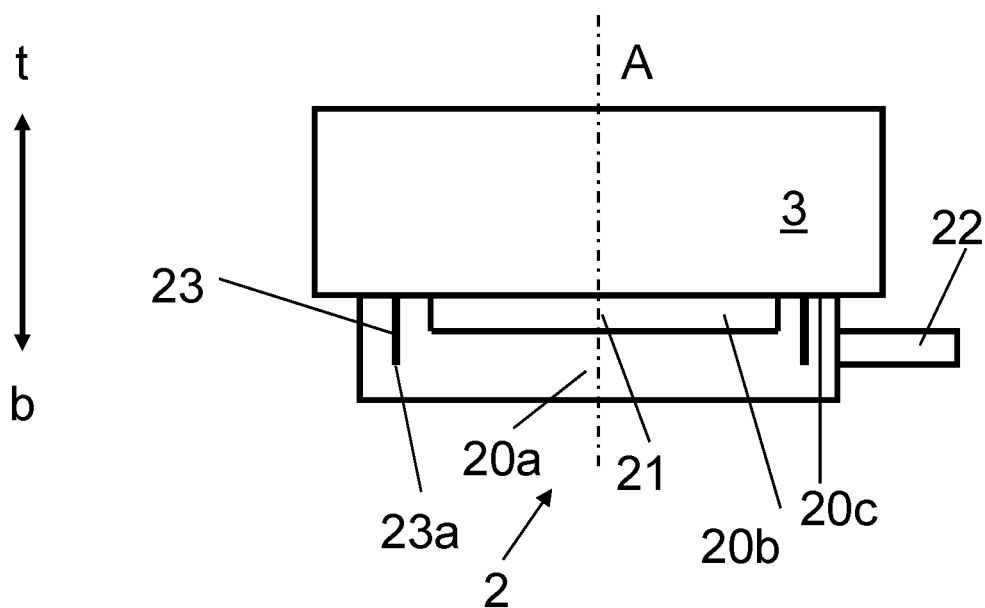
Fig. 1a
Fig. 1b

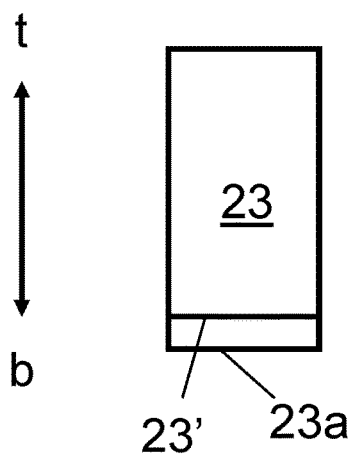
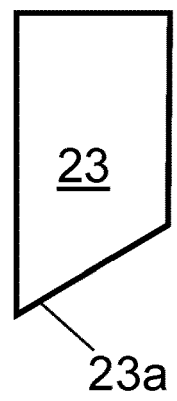
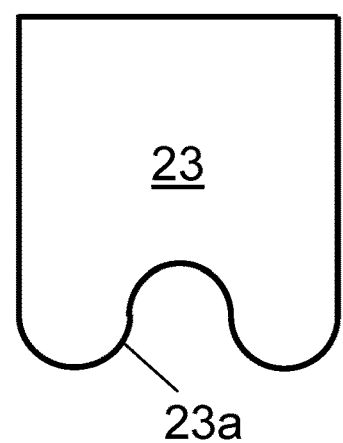
Fig. 3a   Fig. 3b   Fig. 3c
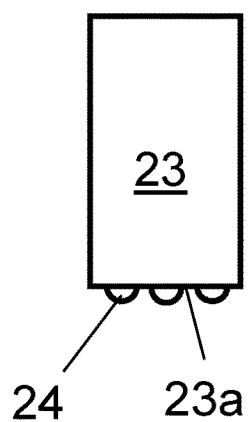
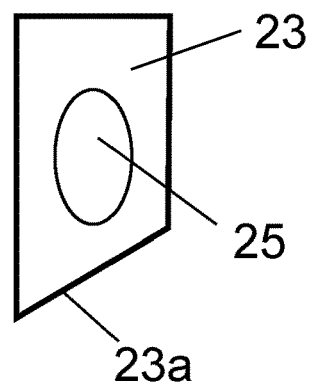
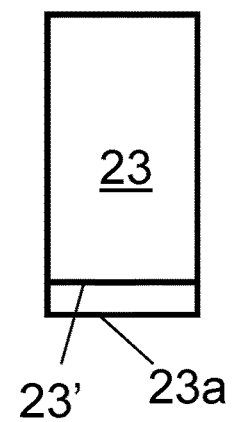
Fig. 3d   Fig. 3e   Fig. 3f
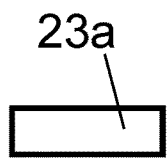
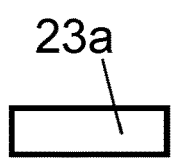
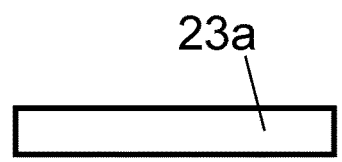
Fig. 4a   Fig. 4b   Fig. 4c
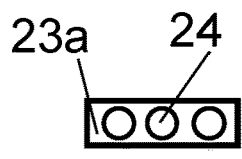
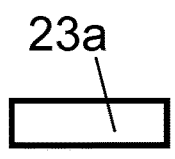
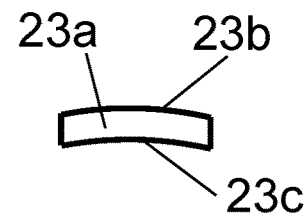
Fig. 4d   Fig. 4e   Fig. 4f

OPHTHALMOLOGICAL PATIENT INTERFACE

The present application claims priority to EP 16199582.4 filed on Nov. 18, 2016, which is hereby incorporated herein by reference in its entirety for all purposes.

TECHNICAL FIELD

The present disclosure relates to devices and methods in the field of ophthalmology. The disclosure relates, in particular, to patient interfaces for coupling an application head to a patient's eye. The disclosure furthermore relates to a method for affixing a patient interface onto a patient eye.

BACKGROUND

The use of radiation generators, in particular lasers, is known for the purposes of treating and/or diagnosing eye tissue. Corresponding devices such as opthalmological laser apparatuses have, for example, a base device with a laser light source for generating laser pulses, for example femtosecond laser pulses, and an application head with a projection lens which is coupled to the patient eye for treatment purposes. The application head can be movably connected to the base device, for example by way of an articulated arm, wherein the articulated arm may simultaneously serve for optical beam guidance from the laser light source to the application head. By way of example, a corresponding arrangement is disclosed in EP 1731120. Moreover, there are devices in which the application head is integrated into the base instrument or in which other device arrangements are provided.

Mechanical and optical coupling of the application head to the patient eye, for example to the cornea and/or sclera of the patient eye, is carried out by way of a patient interface, wherein the patient interface may comprise a transparent contact body, through which the laser pulses emerging from the projection lens are guided and which, by way of the mechanical contact with the cornea, fixes the latter in respect of the patient interface and the projection lens. As an alternative to coupling by means of a contact body, provision can be made of liquid coupling, wherein a coupling liquid, for example a physiological saline solution, is situated between the cornea and the projection lens. By way of example, corresponding patient interfaces are known from WO 2012031277 or EP 2853247. The patient interface can be coupled to the patient eye by means of a vacuum and a negative-pressure cavity of the patient interface. The negative-pressure cavity is typically realized by a suction ring that is placed onto the cornea. Most suction rings have two sealing lips. The lips can be attached to the sclera, the sclera and the cornea, or the cornea only. Furthermore, there are variants which only have one ring and which generate a vacuum over the whole eye, or variants which consist of a plurality of suction chambers/suction cups. The suction ring is the most common method of fastening, but there are also other known solutions. In any case, coupling to the patient eye is carried out by a vacuum or a negative pressure in a negative-pressure cavity of the patient interface, wherein the negative-pressure cavity, along the circumference thereof, abuts on the patient eye in a sealing manner and thereby couples to the patient eye in a fluidically sealing manner and seals the latter from the surroundings. The negative pressure can be generated by a negative-pressure generator, in particular a vacuum pump or a negative-pressure pump. In the known systems, the patient interface is coupled to the application head by means of, for example, a screw-in connection, bayonet closures or vacuum couplings.

SUMMARY OF THE INVENTION

During the application, it is necessary to ensure that the patient interface is connected to the patient eye in a secure and defined manner, and affixed on the latter. An insecure or detaching fixation would have as a consequence that the diagnostic or therapeutic beams emanating from the application head are no longer incident on the patient eye or—in a worst-case scenario—are incident on the patient eye in an undefined or unintended manner. Among others, undesired relative rotation between patient interface and patient eye are a topic of concern.

It has been found that a suction ring with sealing lips that are arranged in a rotationally symmetric manner around a central room, aperture or the like through which the optical beams pass, is particularly favorable because of the resulting uniform contact pressure between suction ring and patient eye. Providing anti-rotation structures at the sealing lips, however, locally reduce the contact pressure and therefore increase the risk of the contact to the eye being lost due to leakage and finally a vacuum loss.

The disclosure provides a patient interface and a method for affixing a patient interface on a patient eye that improves the state of the art regarding secure coupling to the patient eye and preventing relative motion, in particular relative rotation, between patient interface and patient eye. In a general way, this is achieved by the subject of the independent claims. Exemplary as well as particularly favorable embodiments are defined by the dependent claims as well as the present disclosure as a whole.

The disclosure provides a patient interface for

According to an aspect, the overall objective is achieved by providing a patient interface for affixment on onto a patient eye. The patient interface includes a negative pressure cavity with a top wall and a circumferential outer wall. The patient interface further includes an optical passage. The top wall circumferentially surrounds the optical passage. The circumferential outer wall projects from the top wall and circumferentially surrounds the optical passage. The patient interface further includes a number of rib members. The rib members project separately from each other from the top wall into the negative pressure cavity between the circumferential outer wall and the optical passage.

In this document, the expressions "outer" and "inner" are used with respect to a central axis respectively with respect to the center of the patient eye during application. The expressions "top" and "bottom" are used such that that, in a situation of application, the patient interface is arranged on top of the patient eye. Typically, an ophthalmologic application head couples, in a situation of application, to the top side of the patient interface. For allowing suction coupling to the patient eye, the negative pressure cavity is open at its bottom side, such that the patient eye is in direct contact with the inner volume of the negative pressure cavity. The direction defined by "top" and bottom" is further parallel to the central axis, while the direction defined by "outer" and "inner" is radial to the central axis. Generally, the expression "height" is used as a measure between "top" and "bottom" respectively along the central axis. The expression "footprint" refers to a bottom view with a viewing direction from bottom towards top.

At its inner side, the vacuum cavity may be delimited by a circumferential inner wall that extends from the top wall. The circumferential inner wall is typically equidistant from the circumferential outer wall. For typically but not necessarily circular respectively rotational symmetric arrangement, the circumferential outer wall and the circumferential inner wall may in particular be arranged concentrically around the central axis.

The circumferential outer wall and the circumferential inner wall may have the same or different heights. In particular, the circumferential inner wall may have a smaller height than the circumferential outer wall in accordance with the eye curvature. The circumferential inner wall may extend from the top wall parallel to the circumferential outer wall or at an angle with respect to the circumferential inner wall. In particular the circumferential inner wall may be angled away from the circumferential outer wall i. e. towards the central axis. In a variant, the circumferential inner wall is realized as or replaced by a circumferential inner sealing lip. A circumferential outer sealing lip may be provided at the circumferential outer wall.

In application, the circumferential outer wall and the circumferential inner wall or sealing lip contact the eye with their respective circumferential bottom surface that is opposite to the top wall.

The patient interface may further include at least one negative pressure interface, for example a nozzle, for coupling the negative pressure cavity with a negative pressure source.

The favorable effect of the rib members may be understood as follows: In application, the rib members and in particular their eye-contacting bottom surface are, due to the negative pressure inside the negative pressure cavity and the resulting deformation of the patient eye, slightly impressed into the eye tissue, thus resulting in a "positive locking" that prevents the patient interface from moving, in particular rotation, relative to the patient eye. Because of the arrangement of the rib members inside the negative pressure cavity, a uniform sealing contact along the contact of the circumferential outer wall and the eye tissue is maintained.

Additionally, the rib members prevent the patient interface from slipping or sliding relative to the eye surface. According to the state of the art, a circumferential edge is typically present which impresses into the eye tissue and serves for both fluidic sealing and preventing slipping or sliding. Such edge, however, leaves marks on the eye tissue which is generally unfavorable. Via the rib members, preventing slipping or sliding is functionally separated from the fluidic sealing, and the sharp edge is not required.

In an embodiment, the rib members are equally distributed around the optical passage. Such arrangement is advantageous for a symmetric contact pressure distribution and under a general symmetry point of view.

In an embodiment, the rib members are spaced apart, in particular radially spaced apart, from the circumferential outer wall. The rib members being spaced apart from (i. e. not contacting) the circumferential outer wall has the effect that the negative pressure which acts on the negative pressure cavity generates on the circumferential outer wall a sealing respectively contact pressure in a uniform way. The rib members may further be spaced apart, in particularly radially spaced apart, from a circumferential inner wall or circumferential inner sealing lip. With other words, the rib members directly contact the top wall from which they project, but are arranged between and do neither directly contact the circumferential outer wall nor the circumferential inner wall or sealing lip.

In an embodiment, the rib members are arranged equally distant from the circumferential outer wall. For a rotational symmetric arrangement, the rib members may further be arranged equally distant from the circumferential inner wall respectively central axis.

In an embodiment, the optical passage defines a central axis and the rib members extend radially with respect to the central axis. In an alternative embodiment, the rib members are arranged along tangents to a common circumferential curve, the circumferential curve being equidistant to the circumferential outer wall. A tangential arrangement has the particular advantage of a uniform contact pressure along the extension of the rib members.

In an embodiment, a height of the rib members as measured from the top wall varies along a primary extension direction of the rib members.

Generally, the rib members have a height (along the central axis) as explained before, and a width and length perpendicular to the central axis, with the length defining the primary extension direction. While a variety of aspect ratios of length, width and height may be used, the length is normally larger, typically considerably larger, than the width.

In an embodiment, a side view of the rib members is rectangular or trapezoidal. The side view of the rib members is a view perpendicular to the central axis and the primary extension direction. Different arrangements are discussed further below in the context of exemplary embodiments.

In an embodiment, the rib members have co-planar side surfaces, parallel to each other. In an alternative embodiment, the rib members have curved surfaces, such as cylindrically curved surfaces, with the cylinder axes coinciding with or being parallel to the central axis. For such design of the rib members, the inner edge of the eye-contacting bottom surface (adjacent to the circumferential inner wall) and the outer edge of the eye-contacting bottom surface (adjacent to the circumferential outer wall) each substantially extend along a circular contour line on the patient eye surface, which is favorable for a uniform contact pressure.

In an embodiment, the rib members have an eye contact structure on a bottom surface, the bottom surface being opposite to the top wall. The eye contact structure may be realized by a number of dedicated elements, such as burls, pins, protrusions or the like, that project from the bottom surface in bottom direction. The eye contact structure supports the affixation of the patient interface on the patient eye.

In an embodiment, the negative pressure cavity is fluidically through-going, i. e. is realized as single compartment. With a fluidically through-going negative-pressure cavity, a generally uniform negative pressure is achieved over the whole negative pressure cavity. For this purpose, the rib members may be spaced apart, in particularly radially spaced apart from the circumferential outer wall and the circumferential inner wall. Further, the eye-contacting bottom surface of the rib members may be designed such that it does not contact the eye tissue on the whole length of their radial extension.

In alternative embodiments, however, the negative pressure cavity may have a number of two or more fluidically separated compartments. In such an arrangement with a number of compartments, all compartments are favorably charged with negative pressure. Separate negative pressure interfaces may be provided for the compartments.

In an embodiment, the rib members stand back behind a bottom surface of the circumferential outer wall by 0.5 mm to 2.5 mm, for example by 1 mm to 2 mm.

In an embodiment, the number of rib members is between 1 and 50.

In an embodiment, the negative pressure cavity has the shape of a circumferential channel, with the rib members being arranged inside the channel.

In an embodiment, one or more of the circumferential outer wall, the circumferential inner wall and the rib members may be chamfered from outwards to inwards in accordance with the patient eye curvature.

In an embodiment, the patient interface is manufactured from a single piece. Manufacture from a single piece, for example a single piece of plastic, via injection molding, is favorable with respect to tolerances as well as manufacture costs. Such single-piece arrangement can be favorably realized for a patient interface in accordance with the present disclosure.

The disclosure also provides a method for affixing a patient interface on a patient eye. The patient is a patient according to any embodiment as described before and/or further below in the context of exemplary embodiments.

The method includes:
placing the patient interface on the patient eye such that the negative pressure cavity is open to the patient eye;
establishing a negative pressure inside the negative pressure cavity, establishing a fluidic sealing contact between the bottom surface of the circumferential outer wall and the eye, and a pressing contact between the between the rib members and the eye.

A patient interface in accordance with the present disclosure may be affixed on a patient eye by way of a method in accordance with the present disclosure. Disclosed embodiments of a patient interface disclose, at the same time, corresponding embodiments of a method for affixing it. Disclosed method embodiments disclose, at the same time, corresponding patient interface embodiments.

DESCRIPTION OF THE FIGURES

FIG. 1a, 1b show an embodiment of a patient interface in accordance with the present disclosure in a schematic bottom view and side view, respectively.

FIG. 3a-3f show different embodiments of rib members in a schematic bottom view and side view, respectively.

FIG. 4a-4f show the rib members according FIG. 3a-3e in a schematic bottom view.

DETAILED DESCRIPTION

Figure 2A:
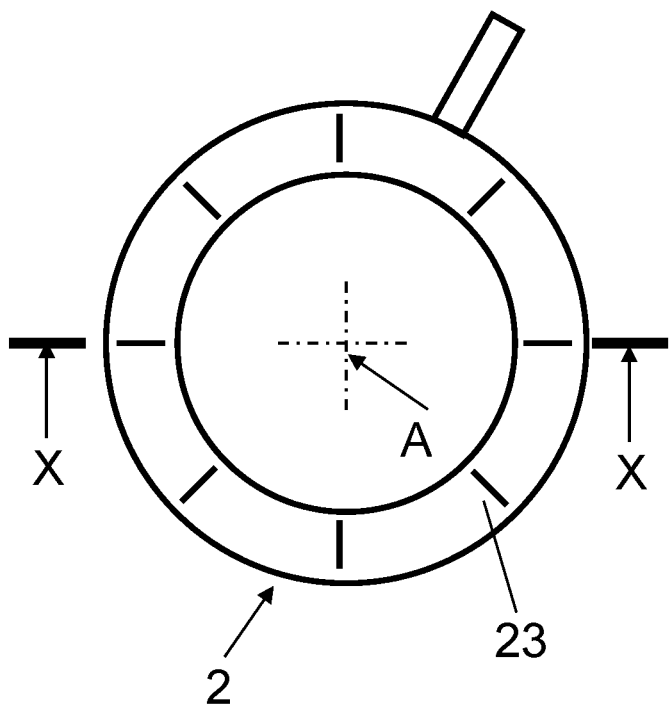
FIG. 2a, 2b show an embodiment of a patient interface in accordance with the present disclosure in a schematic bottom view and side view, respectively.

In the following, exemplary embodiments are discussed in more detail with additional reference to the figures. Generally, identical or substantially identical elements are denoted with the same reference numbers thought the figures and embodiments. Further, elements that are present in more than one figure may not be referenced in each and every figure.

Reference is first made to FIG. 1a, 1b. In FIG. 1a, 1b, reference sign 2 denotes a patient interface in accordance with the present disclosure in a schematic view. FIG. 1a shows the patient interface 2 in schematic bottom view (i. e. with a viewing direction from bottom to top). FIG. 1b shows the patient interface 2 in a schematic sectional view, with the sectional plane being indicated by "X" in FIG. 1a. FIG. 1b further shows an ophthalmologic application head 3, in particular a laser surgical application head, in a schematic view in operative coupling with the top side of the patient interface 2. In FIG. 1b, the top and bottom direction are indicated by "t" and "b", respectively.

The patient interface 2 includes a suction ring of U-shaped cross section, with an outer wall 20a and an inner wall 20b as circumferential walls in concentric arrangement around an axially through-going central room 21. The central room 21 is exemplary rotational symmetric around axis A with a circular footprint and is exemplary of cylindrical shape. In a typical embodiment, the outer diameter of the suction ring is about 20 millimeters. Alternatively, the central room may have a different shape and an for example elliptical footprint. In a variant, the inner wall 20b is realized respectively replaced by a sealing lip of low height. Together with a ring-shaped top wall 20c, the outer wall 20a and the inner wall 20b delimit a negative pressure cavity 20 in form of a circumferential channel with exemplarily U-shaped cross section.

In the application state, the outer wall 20a is placed on and abuts the sclera of the patient eye (not depicted here), while the inner wall 20b is placed on and abuts the limubs. In an alternative arrangement, both the outer wall 20a and the inner wall 20b are placed on and abut the sclera. Further variants where the cornea is contacted partially or entirely are possible as well. Further in the application state, the central room 21 is situated between the corneal surface of the patient eye and the application head 3 such that the cylinder room 21 is delimited by the inner wall 20b as cylinder shell, the cornea as bottom surface and an element of the application head 3 as top surface. The central room 21 can favorably be filled with, for example, physiological saline solution as a coupling liquid. The central room 21 serves as optical passage or aperture for optical beams, such as laser beams, that are emitted from and/or received by the ophthalmologic application head 3.

Alternatively to a through-going central room that is filled with liquid as explained before (liquid coupling), the optical passage may have an optically transparent contact body. In a situation of application, the optical beam, e. g. in form of laser pulses, passes through and is guided by the contact body. Further, the contact body contacts the cornea and fixes it in respect of the patient interface 2 and the ophthalmologic application head 3, in particular a projection lens thereof by way of the mechanical contact with the cornea. This type of patient interface is referred to applanation-type interface.

For affixing the patient interface 2 to the patient eye, a negative pressure or vacuum is generated in the negative pressure cavity 20 and a negative pressure or vacuum thus fixes the patient interface 2 on the patient eye. For applying the negative pressure, the patient interface 2 further includes negative pressure interface, exemplarily shown as elongated hollow connection nozzle 22. The negative pressure interface 22 opens into the negative pressure cavity 20 via a corresponding negative pressure aperture in the outer wall 20a. The nozzle 22 is designed for coupling with a negative pressure device, such as a suction pump, via a corresponding negative pressure supply line (tubing) as generally known in the art.

Inside the negative pressure cavity 20, a number of exemplarily eight rib members 23 is arranged. Typically, all rib members 23 are of identical design. The rib members 23 project separately from the top wall 20c into the negative pressure cavity 20. In this embodiment, the rib members 23 are arranged equally distant from the outer wall 20a (in particular equally distant from the cylindrical inner surface of the outer wall 20a). Exemplarily, the rib members 23 are equally distributed around the central axis A. Further in this embodiment, the rib members 23 are arranged along tangents to a common circumferential curve, the circumferential curve being equidistant to the circumferential outer wall. In this embodiment with a cylindrical inner room 21, the circumferential curve is further equidistant to the central axis A and is defined by a circle around the central axis A that touches the middle of the inner sides of the rib members 23. Further exemplarily, the rib members 23 extend parallel to the outer wall 20a, the inner wall 20b and the central axis A.

The height of the circumferential outer wall 20a is larger than the height of the circumferential inner wall 20b. The height of the rib members 23 is in-between the height of the circumferential outer wall 20a and circumferential inner wall 20b, such that the bottom surfaces of all of the circumferential outer wall 20a, the circumferential inner wall 20b, and the rib members 23 contact the curved outer surface of the patient eye.

In a side view (perpendicular to the central axis A), the rib members 23 are exemplarily rectangular, with a height (measured from the top wall 20c towards the open bottom of the negative pressure cavity 20) being smaller than a height of the top wall 20c and, in this example, the inner wall 20b. As clearly visible in FIG. 1b, the rib members 20a stand back behind the eye-contacting bottom surface of the outer wall 20a, and, in this example, the inner wall 20b. The rib members 23 are accordingly fully arranged with the negative pressure cavity 21.

Figure 5:
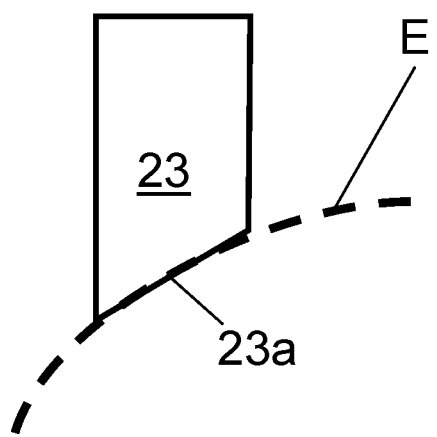
FIG. 5 shows a rib member contacting an eye in accordance with the present disclosure.

In application, the rib members 23 and in particular their eye-contacting bottom surface 23a (as shown in FIG. 5) are, due to the negative pressure inside the negative pressure cavity 21 and the resulting deformation of the patient eye, slightly impressed into the eye tissue, thus resulting in a "positive locking" that prevents the patient interface from moving, in particular rotation, relative to the patient eye.

Figure 2B:
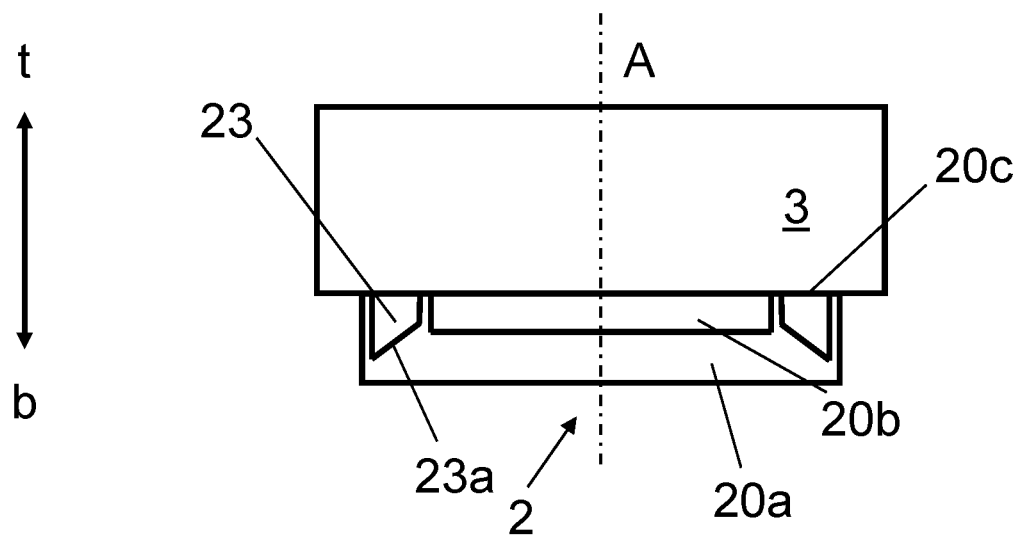

In the following, reference is additionally made to FIG. 2a, 2b, illustrating a further embodiment of a patient interface 2 in accordance with the present disclosure. The embodiment of FIG. 2a, 2b is similar the embodiment of FIG. 1a, 1b as discussed before. In contrast to the latter, however, the rib members 23 are designed and arranged differently. Here, the rib members 23 extend radially with respect to the central axis A. The rib members 23 are radially spaced apart from the outer wall 20a and the inner wall 20b. The rib members 23 of this embodiment are of a trapezoidal side view, resulting in the eye-contacting bottom surface substantially corresponding to the curved eye surface.

In the following, reference is additionally made to FIG. 3a-3e and FIG. 4a-4e. FIG. 3a-3e show different embodiments of a rib member 23 in a schematic side view. In each of FIG. 3a-3e, the connection to the top wall 20C (not shown) is opposite to the eye-contacting bottom surface 23a. FIG. 5 shows rib member 23 with eye-contacting bottom surface 23a in contact with an eye E. FIG. 4a-4e show the corresponding bottom views, i. e. a view onto the eye-contacting bottom surface 23a.

The embodiment of the rib member 23 in FIG. 3a, 4a corresponds to the embodiment of the patient interface 2 as shown in FIG. 1a, 1b and is particularly suited for a tangential arrangement. It can be seen that both the side view and the bottom view may be substantially rectangular. As indicated by edge 23', the rib members are optionally chamfered such that the height of the rib members 23 is somewhat lower at the inner side (facing the circumferential inner wall 20b) as compared to the outer side (facing the circumferential outer wall 20a), in accordance with the eye tissue curvature.

The embodiment of the rib member 23 in FIG. 3b, 4b corresponds to the embodiment of the patient interface 2 as shown in FIG. 2a, 2b and is particularly suited for a radial arrangement.

In the embodiment of FIG. 3c, FIG. 4c, the height of the rib member 23 is varied along its length, such that the side view of the eye-contacting bottom surface 23a is waved. Thereby, an eye contact structure is established and the amount by which the rib member 23 is impressed into the eye tissue is increased. In this way, the before-explained positive locking is improved.

In the embodiment of FIG. 3d, FIG. 4d, an eye contact structure is realized by way of a number of burls 24 that are arranged along the length of the rib member 23 and project from the generally plane eye-contacting bottom surface 23a in bottom direction.

The embodiment of FIG. 3e, 4e, is similar to the embodiment of FIG. 3b, 4b, but has one or more through-going negative pressure coupling apertures 25. The negative-pressure coupling apertures 25 support the establishment of a uniform negative pressure inside the negative-pressure cavity 20. Furthermore, they are favorable in situations where other fluidic paths, in particular a gap between a rib member 23 and the circumferential outer wall 20a respectively circumferential inner wall 20b, is partly or fully blocked, for example by tissue or liquid. Negative-pressure coupling apertures may also be provided for any of the other member designs.

The embodiment of FIG. 3f, 4f is similar to the embodiment of FIG. 3a, 4a and may also be used in a tangential arrangement as shown in FIG. 1a, 1b. In contrast to the embodiment of FIG. 3a, 4a, however, the inner surface 23c (facing the circumferential inner wall 20b) and the outer surface 23b (facing the circumferential outer wall 20a) are cylindrically curved and typically concentric with respect to the central axis A. As compared to the embodiment of FIG. 3a, 4b, this arrangement results in a more uniform contact pressure between eye-contacting bottom surface 23a and eye tissue.

Favorably, a patient interface 2 may, including the rib members 23, be manufactured as a single piece e. g. via injection moulding, or via 3D printing.

The invention claimed is:

1. Patient interface for affixment onto a patient eye, said patient interface comprising:
   a negative pressure cavity with a top wall and a circumferential outer wall;
   an optical passage, wherein the top wall circumferentially surrounds the optical passage and wherein the circumferential outer wall projects from the top wall and circumferentially surrounds the optical passage;
   a number of rib members, the rib members projecting separately from each other f from the top wall into the negative pressure cavity between the circumferential outer wall and the optical passage; and
   wherein each rib member comprises an eye-contacting bottom surface.

2. Patient interface according to claim 1, wherein the rib members are equally distributed around the optical passage.

3. Patient interface according to claim 1, wherein the rib members are spaced apart from the circumferential outer wall.

4. Patient interface according to claim 3, wherein the rib members are arranged equally distant from the circumferential outer wall.

5. Patient interface according to claim 1, wherein the optical passage defines a central axis and the rib members extend radially with respect to the central axis.

6. Patient interface according to claim 1, wherein the rib members are arranged along tangents to a common circumferential curve, the common circumferential curve being equidistant to the circumferential outer wall.

7. Patient interface according to claim 1, wherein a height of the rib members as measured from the top wall varies along a primary extension direction of the rib members.

8. Patient interface according to claim 1, wherein a side view of the rib members is rectangular or trapezoidal in shape.

9. Patient interface according to claim 1, wherein the rib members have an eye contact structure on a bottom surface, the bottom surface being opposite to the top wall.

10. Patient interface according to claim 1, wherein the negative pressure cavity is fluidically through-going.

11. Patient interface according to claim 1, wherein the rib members stand back behind a bottom surface of the circumferential outer wall by 0.5 mm to 2 mm.

12. Patient interface according to claim 1, wherein the number of rib members is between 1 and 50.

13. Patient interface according to claim 1, wherein the negative pressure cavity has the shape of a circumferential channel, with the rib members being arranged inside the circumferential channel.

14. Patient interface according to claim 1, wherein the patient interface is a single piece of plastic.

15. Method for affixing a patient interface on a patient eye, the method comprising:
   providing the patient interface, wherein the patient interface comprises:
   a negative pressure cavity with a top wall and a circumferential outer wall,
   an optical passage, wherein the top wall circumferentially surrounds the optical passage and wherein the circumferential outer wall projects from the top wall and circumferentially surrounds the optical passage, and
   a number of rib members, the rib members projecting separately from each other from the top wall into the negative pressure cavity between the circumferential outer wall and the optical passage, wherein each rib members comprises an eye-contacting bottom surface;
   placing the patient interface in the patient eye such that the negative pressure cavity is open to the patient eye; and
   establishing a negative pressure inside the negative pressure cavity, establishing a fluidic sealing contact between the eye-contacting bottom surface of the circumferential outer wall and the eye, and a pressing contact between the rib members and the patient eye.

16. The method of claim 15, wherein the rib members are equally distributed around the optical passage.

17. The method of claim 15, wherein the rib members are spaced apart from the circumferential outer wall.

18. The method of claim 15, wherein the negative pressure cavity has the shape of a circumferential channel, with the rib members being arranged inside the circumferential channel.

19. An apparatus comprising:
   a negative pressure cavity with a top wall and a circumferential outer wall;
   an optical passage, wherein the top wall circumferentially surrounds the optical passage and wherein the circumferential outer wall projects from the top wall and circumferentially surrounds the optical passage; and
   a number of rib members, the rib members projecting separately from each other from the top wall into the negative pressure cavity between the circumferential outer wall and the optical passage,
   wherein the rib members are equally distributed around the optical passage,
   wherein a height of the rib members as measured from the top wall varies along a primary extension direction of the rib members,
   wherein each rib member comprises an eye-contacting bottom surface.

* * * * *